(12) United States Patent
Perrin et al.

(10) Patent No.: US 12,310,659 B2
(45) Date of Patent: May 27, 2025

(54) METHOD FOR ASSESSING THE SUITABILITY BETWEEN AN OPTICAL DEVICE AND A USER OF THE OPTICAL DEVICE

(71) Applicant: ESSILOR INTERNATIONAL, Charenton-le-Pont (FR)

(72) Inventors: Jean-Luc Perrin, Charenton-le-Pont (FR); Thierry Laloux, Charenton-le-Pont (FR); Damien Paille, Charenton-le-Pont (FR)

(73) Assignee: Essilor International, Charenton-le-pont (FR)

( * ) Notice: Subject to any disclaimer, the term of this patent is extended or adjusted under 35 U.S.C. 154(b) by 981 days.

(21) Appl. No.: 17/415,273

(22) PCT Filed: Dec. 16, 2019

(86) PCT No.: PCT/EP2019/085374
§ 371 (c)(1),
(2) Date: Jun. 17, 2021

(87) PCT Pub. No.: WO2020/127068
PCT Pub. Date: Jun. 25, 2020

(65) Prior Publication Data
US 2022/0022742 A1  Jan. 27, 2022

(30) Foreign Application Priority Data
Dec. 18, 2018 (EP) .................................... 18306724

(51) Int. Cl.
*A61B 3/09* (2006.01)
*A61B 3/04* (2006.01)
*A61B 5/00* (2006.01)

(52) U.S. Cl.
CPC ............... *A61B 3/09* (2013.01); *A61B 3/04* (2013.01); *A61B 5/746* (2013.01)

(58) Field of Classification Search
CPC .... A61B 3/09; A61B 3/04; A61B 3/02; A61B 3/0033; A61B 3/113; A61B 3/00;
(Continued)

(56) References Cited

U.S. PATENT DOCUMENTS

2011/0170058 A1  7/2011  Suzuki et al.
2014/0347265 A1  11/2014  Aimone et al.
(Continued)

OTHER PUBLICATIONS

International Search Report for PCT/EP2019/085374 dated May 13, 2020, 5 pages.
(Continued)

*Primary Examiner* — Travis S Fissel
(74) *Attorney, Agent, or Firm* — NIXON & VANDERHYE

(57) ABSTRACT

Disclosed is a computer-implemented method for assessing suitability between an optical device and its user, the optical device including an optical lens placed in front of an eye of the user when the user uses the optical device, the optical lens having a plurality of optical zones having different optical functions, the method including at least the following steps: a requesting step, during which the user, equipped with the optical device, is requested to use the optical device in a plurality of different visual situations, each visual situation being associated with an optical zone of the optical lens and during which the user looks at a visual target located in the user's natural environment through the optical lens; and a suitability index assessing step, during which the user assesses a suitability index based on his use of the optical device in the plurality of different visual situations.

14 Claims, 3 Drawing Sheets

(58) Field of Classification Search
CPC ... A61B 3/0016; A61B 3/0025; A61B 3/0083;
A61B 3/022; A61B 3/06; A61B 3/066;
A61B 3/08; A61B 3/085; A61B 3/10;
A61B 3/18; A61B 5/746; G02C 7/025;
G02C 7/061; G02C 13/005
USPC ....... 351/200, 203, 205, 209, 222, 223, 246,
351/206
See application file for complete search history.

(56) References Cited

U.S. PATENT DOCUMENTS

| 2015/0248020 | A1 | 9/2015 | Fayolle |
| 2017/0017083 | A1* | 1/2017 | Samec ................ A61B 3/0008 |
| 2017/0090204 | A1 | 3/2017 | Lebrun et al. |

OTHER PUBLICATIONS

Written Opinion of the ISA for PCT/EP2019/085374 dated May 13, 2020, 9 pages.

* cited by examiner

METHOD FOR ASSESSING THE SUITABILITY BETWEEN AN OPTICAL DEVICE AND A USER OF THE OPTICAL DEVICE

CROSS-REFERENCE TO RELATED APPLICATIONS

This application is the U.S. national phase of International Application No. PCT/EP2019/085374 filed Dec. 16, 2019 which designated the U.S. and claims priority to European Application No. 18306724.8 filed Dec. 18, 2018, the entire contents of each of which are hereby incorporated by reference.

FIELD OF THE INVENTION

The present invention relates to a method for assessing the suitability between an optical device and a user of the optical device. The invention further relates to a computer program and a computer readable medium.

BACKGROUND OF THE INVENTION

Ophthalmic lenses intended to be held in a frame usually involve a prescription. The ophthalmic prescription can include a positive or negative power prescription as well as an astigmatism prescription. These prescriptions correspond to corrections enabling the wearer of the lenses to correct defects of his vision. A lens is fitted in the frame in accordance with the prescription and with the position of the wearer's eyes relative to the frame.

For presbyopic wearers, the value of the power correction is different for far vision and near vision, due to the difficulties of accommodation in near vision.

The prescription thus comprises a far-vision power value and an addition representing the power increment between far vision and near vision; this comes down to a far-vision power prescription and a near-vision power prescription. Lenses suitable for presbyopic wearers are often progressive addition lenses.

Progressive addition ophthalmic lenses include a far-vision zone, a near-vision zone and an intermediate-vision zone, a principal progression meridian crossing these three zones. They are generally determined by optimization, based on a certain number of constraints imposed on the different features of the lens.

Nevertheless, progressive addition lenses (PAL) generate aberrations, notably leading to blur, that in particular reduce the field of view and distortion that creates for example the well-known swim effect. The design of the lens is necessarily a compromise between these aberrations.

Consequently, some wearers may have difficulties to adapt to the use of progressive addition lenses despite normal binocular vision and other normal clinical findings. Thus, wearing progressive addition lenses requires often from the wearers a learning phase to change their visual and/or visuo-motor behaviour and/or their perception of space, their acceptance of distortions like residual astigmatism, optical aberrations . . . .

Nevertheless, in some cases, getting used to progressive addition lenses might not succeed because of problems linked to this learning phase. For example, the wearer can have a wrong use of the lens, i.e. he/she uses the inappropriate zones of the lens or he/she adopts a wrong posture. Despite the learning phase, the wearer does not adapt to the distortions or the wearer lacks motivation within progressive addition lenses use.

Unfortunately, the wearer might not understand the causes of the troubles. Thus, he/she might think the problems he/she is encountering are his/her fault, and thus, he/she might not come back to his eye care professional (ECP). Consequently, the wearer will continue using the lenses in a bad way (wrong zone usage, wrong posture . . . ) or quit wearing to progressive addition lenses.

There is a need for simple and reliable method to assess the suitability between an optical device and a user of the optical device and to help the person to adapt or not to the use of progressive addition lenses.

SUMMARY OF THE INVENTION

To this end, the invention proposes a method, implemented by computer means, for assessing the suitability between an optical device and a user of the optical device, the optical device comprising at least an optical lens configured to be placed in front of at least an eye of the user when the user uses the optical device, the at least optical lens having a plurality of optical zones having different optical functions, the method comprising at least the following steps:

a requesting step, during which the user, equipped with the optical device, is requested to use the optical device in a plurality of different visual situations, each visual situation being associated with an optical zone of the optical lens and during which the user looks at a visual target located in the user's natural environment through the optical lens; and a suitability index assessing step, during which the user assesses a suitability index based on his use of the optical device in the plurality of different visual situations.

Advantageously, such a method for assessing the suitability between an optical device and a user of the optical device provides simple and reliable method to help the person to adapt or not to the use of progressive addition lenses. Thanks to the invention, the assessment of the use of the optical device, as a progressive addition lenses and acceptance is not based on a single criterion but on a global appreciation of the user. Indeed, this assessment of the use of the optical device is linked to his/her ability to make the right head movements and/or right eye movements and/or to his/her ability to accept distortions like residual astigmatism, optical aberrations . . . .

Moreover, the assessment is based on the user's natural environment and not on an artificial setup or only on screens.

According to further embodiments which can be considered alone or in combination:

the method further comprises:
  repeating the requesting step and the suitability index assessing step at least on a weekly basis; and
  storing the evolution over time of the suitability index;
the method further comprises:
  a comparison step, during which the assessed suitability index is compared to a predetermined threshold value; and
  a recommendation providing step, during which a recommendation is provided to the user based on the result of the comparing step and/or on the evolution over time of the suitability index;

the method further comprises information providing step, during which information is provided to a professional based on the result of the comparing step;
the comparison step further comprises:
a second comparison step, during which if the assessed suitability index is much lower than the predetermined threshold value, the assessed suitability index is compared to a critical threshold value; and
an alert providing step, during which an alert is provided to the user and/or to a professional based on the result of the second comparing step;
the professional is an eye care professional (ECP) or an eyeglasses manufacturer;
the provided recommendation to the user comprises data on how to suitably use the optical device;
the suitability index assessing step comprises at least a subjective assessing step, during which a subjective assessment is provided, the subjective assessment being related to:
the level of comfort of the user during the use of the optical device in the plurality of different visual situations; and/or
the level of fatigue of the user during the use of the optical device in the plurality of different visual situations; and/or
the level of difficulty of the user to use the optical device in the plurality of different visual situations;
the suitability index assessing step comprises at least a measurement step, during which a physiological parameter indicative is measured, the physiological parameter being indicative of the physiology of the user during the use of the optical device in the plurality of different visual situations;
the suitability index assessing step comprises at least a visual performance determining step, during which a level of visual performance of the user is determined during the use of the optical device in the plurality of different visual situations;
the suitability index assessing step comprises at least an environmental parameter determining step, during which an environmental parameter relative to the parameter of the environment of the user is determined during the use of the optical device in the plurality of different visual situations, and wherein the level of visual performance of the user is determined based on the environmental parameter;
for each different visual situations of the plurality of different visual situations, the user equipped with the optical device is requested to use the optical device during a given duration;
the request is generated and/or sent by a distant unity;
the optical device is one of the ophthalmic devices comprised in the list consisting of:
a progressive addition lens,
a bifocal lens,
a multifocal lens,
a mid-distance lens,
a lens having a tint gradient,
an augmented reality eyewear,
a single vision lens having different astigmatism correction for near and far visions.

According to a further aspect, the invention further relates to a device comprising a processor adapted to store one or more sequence of instructions and to carry out at least one of the steps of the method according to the invention.

More particularly, the invention relates to a computer program product comprising one or more stored sequences of instructions that are accessible to a processor and which, when executed by the processor, causes the processor to carry out the steps of the method according to the invention.

The invention further relates to a computer readable medium carrying one or more sequences of instructions of the computer program product according to the invention.

Unless specifically stated otherwise, as apparent from the following discussions, it is appreciated that throughout the specification discussions utilizing terms such as "computing", "calculating", or the like, refer to the action and/or processes of a computer or computing system, or similar electronic computing device, that manipulate and/or transform data represented as physical, such as electronic, quantities within the computing system's registers and/or memories into other data similarly represented as physical quantities within the computing system's memories, registers or other such information storage, transmission or display devices.

Embodiments of the present invention may include apparatuses for performing the operations herein. This apparatus may be specially constructed for the desired purposes, or it may comprise a general purpose computer or Digital Signal Processor ("DSP") selectively activated or reconfigured by a computer program stored in the computer. Such a computer program may be stored in a computer readable storage medium, such as, but is not limited to, any type of disk including floppy disks, optical disks, CD-ROMs, magnetic-optical disks, read-only memories (ROMs), random access memories (RAMs) electrically programmable read-only memories (EPROMs), electrically erasable and programmable read only memories (EEPROMs), magnetic or optical cards, or any other type of media suitable for storing electronic instructions, and capable of being coupled to a computer system bus.

The processes and displays presented herein are not inherently related to any particular computer or other apparatus. Various general purpose systems may be used with programs in accordance with the teachings herein, or it may prove convenient to construct a more specialized apparatus to perform the desired method. The desired structure for a variety of these systems will appear from the description below. In addition, embodiments of the present invention are not described with reference to any particular programming language. It will be appreciated that a variety of programming languages may be used to implement the teachings of the inventions as described herein.

BRIEF DESCRIPTION OF THE DRAWINGS

Embodiments of the invention will now be described, by way of example only, and with reference to the following drawings in which.

Elements in the figures are illustrated for simplicity and clarity and have not necessarily been drawn to scale. For example, the dimensions of some of the elements in the figure may be exaggerated relative to other elements to help improve the understanding of the embodiments of the present invention.

DETAILED DESCRIPTION

Figure 1:
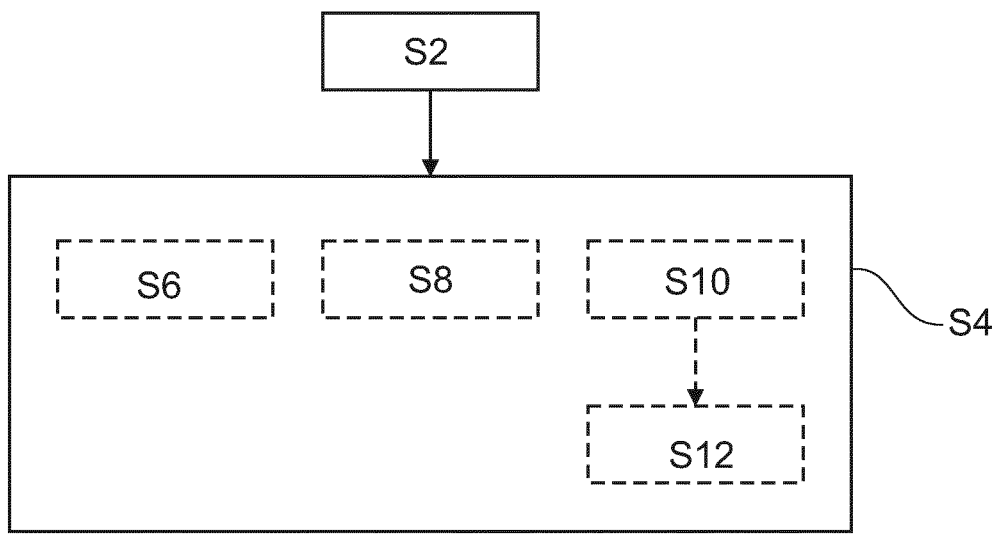
FIG. 1 is a flowchart of the steps of an embodiment of the method for assessing the suitability between an optical device and a user of the optical device according to the invention.

With reference to FIG. 1, the invention relates to a method, implemented by computer means, for assessing the suitability between an optical device and a user of the optical device.

In the sense of the invention, the suitability between an optical device and a user of the optical device is the positive or negative appreciation of the use of the optical device by the user that is the result of the combination of:
- the parameters of the optical device, comprising the optical characteristics, the position relatively to the user, the mechanical characteristics, and any other characteristics of the optical device that might modify the perception or the comfort of the user; and
- the behavior, mental and perceptual processes of the user.

A perceptual process is a process for re-creating mentally an object of the real world, which stimulates the body's sensory organs by means of light, sound or another physical process. These sensory organs transform the input energy into neural activity which is then transmitted to the brain for the mental re-creation.

A high level of suitability corresponds to a situation where the user perceives the maximum of visual information without negative counterparts (postural demand, high concentration level, needed time for adjusting, dizziness, unacceptance of the lens, high amount of blur or distortions perceived . . . ).

A low level of suitability corresponds to a situation where the user perceives few visual information, and/or at the cost of high negative counterparts.

The optical device comprises at least an optical lens configured to be placed in front of at least an eye of the user when the user uses the optical device.

Furthermore, the optical lens has a plurality of optical zones having different optical functions. For example, the optical device is an ophthalmic device such like a progressive addition lens, a bifocal lens, a multifocal lens, a mid-distance lens having no correction for far vision, a lens having a tint gradient, an augmented reality eyewear or a single vision lens having different astigmatism correction for near and far visions.

The method comprises at least a requesting step S2 and a suitability index assessing step S4.

During the step S2, the user, equipped with the optical device, is requested to use the optical device in a plurality of different visual situations, during which the user looks at a visual target located in the user's natural environment through the optical lens.

In the sense of the invention, the natural environment of the user is a set of objects for which their shapes, textures and colors as well as their positions, directions and movements relatively to the user's eyes and as the context where their appear that have a high probability to occur within the user's daily activities (at his home, during is working hours, during his commuting time, etc.). More particularly, the natural environment of the user does not refer to an artificial setup (constrained to the eye care practitioner office) or to only screens.

For example, if the optical device comprises a near vision zone, an intermediate vision zone and a far vision zone, such like a progressive addition lens, the user of this progressive addition lens is asked to look successively at visual targets located in his/her natural environment through the different optical zones of the optical lens. Thus, the user is asked to look at his smartphone which is located at near distance in order to look through the near vision zone of the optical lens. In order to look through the intermediate vision zone of the optical lens, the user can be asked to look at his/her desktop computer, and to use the distance vision zone of the optical lens, the user can be asked to look at a tree in front of him/her or a building on his/her side even if the user looks at them through a window.

Thus, after having received the basics learning for the use of progressive addition lens, for example, the user is put in a situation where he/she has to look successively through different zones of his/her lenses at objects at different distances. For example, the basics learning comprises the correct use of each zone of the optical lens, i.e. the correct posture to have and the appropriate zone of the lens to look through for objects at near distance, intermediate distance and/or far distance.

According to another example, if the optical device is a mid-distance lens(es) or middle-distance lens, i.e. having no correction for far vision, the user can be asked to look over his/her lens(es) to see well an object at far distance.

Preferably, the user equipped with the optical device is requested to use the optical device during a given duration, for example at least 5 seconds, for each different visual situations of the plurality of different visual situations. In addition, the user equipped with the optical device is requested to use the optical device several times, for example at least 5 times, for each visual targets. The order of presentation is advantageously randomly chosen.

Advantageously, the request is generated and/or sent by a distant unity.

For example, the user can download a computer program, as an application, on his/her own phone or computer just after having bought progressive lenses.

The application can release a signal, as a picture and/or a sound and/or a vibration, when the user has to look at a new visual target through the optical lens.

Alternatively, the application can let the user tap on the screen when he/she feels he/she managed to see clearly the visual target, and then display the next one.

Of course, the number of visual targets/situations depends preferably on the number of different optical zones the optical lens has.

Then, the user assesses a suitability index based on his/her use of the optical device in the plurality of different visual situations during the suitability index assessing step S4.

Thus, at the end of the step S2, the user is asked to rate his/her use of the optical device in the plurality of different visual situations, for example on a scale from 1 to 10.

More particularly, according to an embodiment of the invention, the suitability index assessing step S4 comprises at least a subjective assessing step S6, during which a subjective assessment is provided, the subjective assessment being related to:
- the level of comfort of the user during the use of the optical device in the plurality of different visual situations; and/or
- the level of fatigue of the user during the use of the optical device in the plurality of different visual situations; and/or the level of difficulty of the user to use the optical device in the plurality of different visual situations.

Advantageously, the subjective assessment can be done on the different optical zones of the optical lens in order to distinguish the levels of comfort of the user during the use of the optical device in near vision, intermediate vision and far vision.

The subjective assessment can also be relative to a level of perceived effort to complete the task required.

According to another example, the subjective assessment can also be relative to a level of comfort during looking at the object versus a level of comfort during switching from one optical zone to another and/or a level of comfort of vision versus a level of postural comfort.

According to another embodiment of the method compatible with the previous one, the suitability index assessing step S4 comprises at least a measurement step S8. During the at least one measurement step S8, a physiological parameter is measured. The physiological parameter is indicative of the physiology of the user during the use of the optical device in the plurality of different visual situations.

For example, in addition to or instead of a declarative rating, a neural indicator of cognitive load or emotion of the user during the use of the optical device in the plurality of different visual situations can be measured, such like an electroencephalogram (EEG), a functional near-infrared imaging (fNIR), an electro-dermal potential, a heart rate . . . .

According to another embodiment of the method compatible with the previous ones, the suitability index assessing step S4 comprises at least a visual performance determining step S10.

During the at least one visual performance determining step S10, a level of visual performance of the user is determined during the use of the optical device in the plurality of different visual situations.

For example, a visual acuity, a contrast sensitivity or a reading speed can be determined during the use of the optical device in the plurality of different visual situations.

Figures 2A, 2B:
FIGS. 2A, 2B illustrate the measurement of successive positions of the gaze of the user within the optical device during stabilization between two optical zones of the optical device.

According to another example, if the optical device is equipped with an eye tracking system, the optical device can measure the time and/or the path for the eyes of the wearer to stabilize or the amount of "parasite" eye movements between starting position P1 and final position P2, in order to switch between two optical zones of the optical lens as illustrated on FIGS. 2A-2B. Indeed, FIG. 2A illustrates the best path for the eyes of the wearer to stabilize between starting position P1 and final position P2 which is preferable versus "parasite" eye movements between both positions P1 and P2 represented on FIG. 2B.

According to another example, if the optical device is equipped with a camera, the optical device can measure the distance with the visual targets in order to advantageously verify that the visual targets are in a correct set-up for far, intermediate and close distances.

More particularly, the suitability index assessing step S4 can further comprise at least an environmental parameter determining step S12, during which an environmental parameter relative to a parameter of the environment of the user is determined during the use of the optical device in the plurality of different visual situations. The level of visual performance of the user is thus determined based on the environmental parameter.

For example, the parameter of the environment of the user determined is the distance to the observed visual target.

According to another example, the parameter of the environment of the user determined is the level of luminosity of the environment.

Such information can help an eye care professional to adapt his/her recommendation to better use the optical device for example.

Figure 3A:
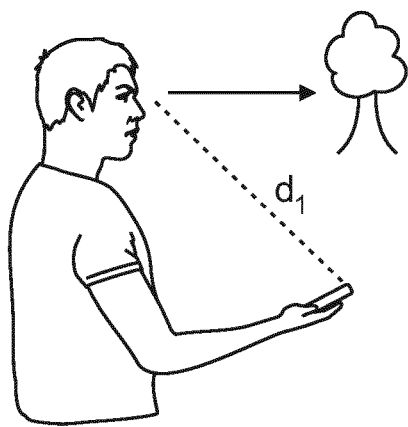
FIGS. 3A to 3E illustrate the measurement of the time for the eyes of a user to stabilize between two visual situations.
Figure 3B:
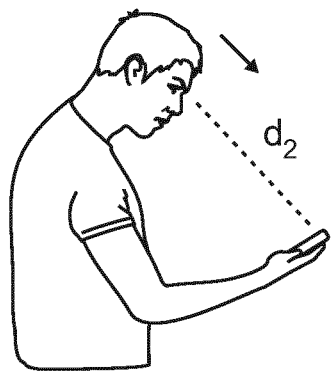
Figure 3C:
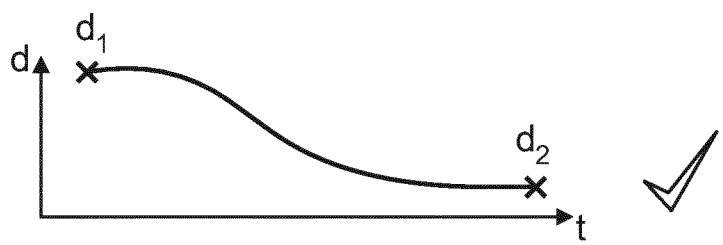
Figure 3D:
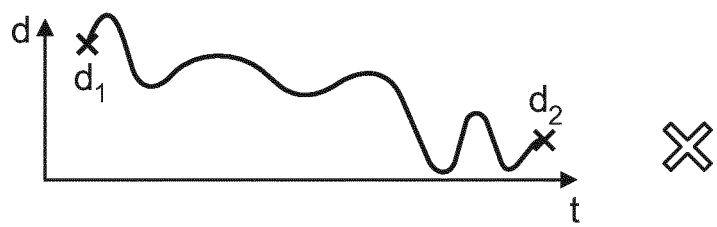
Figure 3E:
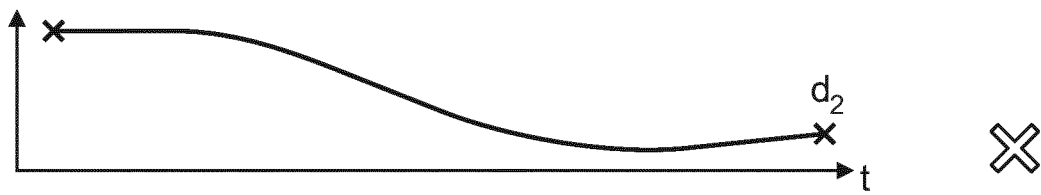

Thus, according to an example, if the optical device is equipped with a sensor for measuring the distance between the eyes and a screen of a smartphone for example, the optical device can measure the time for the eyes of the wearer to stabilize between a first position and a second position respectively illustrated on FIGS. 3A and 3B. Between both positions 3A, 3B, the user is requested to look at a far target for example a tree in front of him/her. FIG. 3C illustrates the best "path" for the eyes of the user to stabilize between the first position P1 and the second position P2 which is preferable versus "parasite" eye movements between both positions P1 and P2 represented on FIG. 3D. FIG. 3E illustrates a long time stabilization to the second position P2.

Advantageously, the requesting step S2 and the suitability index assessing step S4 are repeated at least on a weekly basis and the evolution over time of the suitability index is stored in a storing means, for example a memory.

For example, the user is requested to repeat the requesting step S2 and the suitability index assessing step S4 on several days, and at least one time per day.

Alternatively, the user can perform the task several times on the first day.

Figure 4:
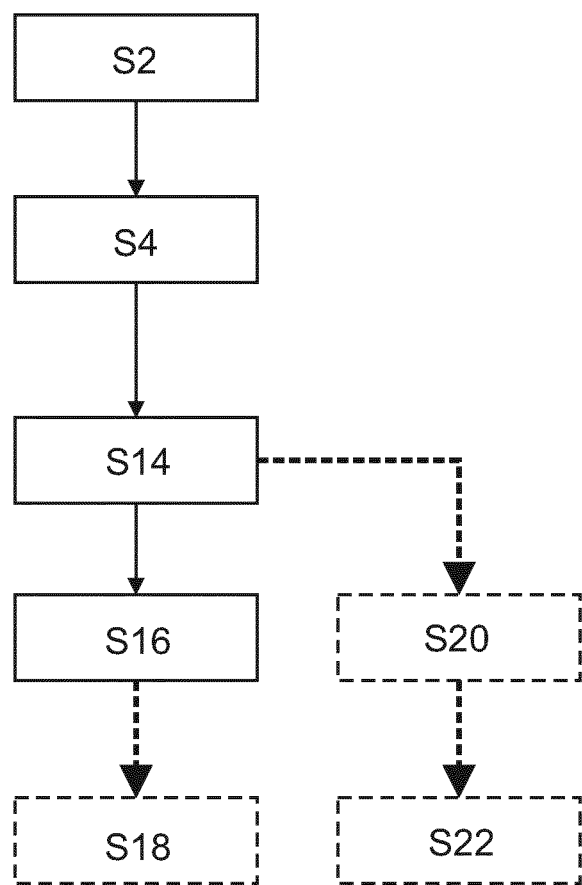
FIG. 4 is a flowchart of the steps of another embodiment of the method for assessing the suitability between an optical device and a user of the optical device according to the invention.

As illustrated on FIG. 4 which illustrates another embodiment compatible with the previous ones, the method can further comprise a comparison step S14 and a recommendation providing step S16.

During the step S14, the assessed suitability index is compared to a predetermined threshold value.

Then, a recommendation is provided to the user based on the result of the comparing step and/or on the evolution over time of the suitability index during the step S14.

For example, if the suitability index is extremely low on the first day, the user can be directly directed toward his/her eye care professional (ECP).

Preferably, the provided recommendation to the user comprises data on how to suitably use the optical device.

According to another example, if the user's suitability indexes are below the predetermined threshold after several days, he/she is asked to visit again his/her eye care professional in order to understand and solve problems.

The recommendation can be provided through the computer program, for example the information (address and/or phone number) relative to an optician is displayed and the user can directly call him/her.

According to another example, when coming back to the eye care professional, the user can show him/her the evolution over time of the suitability index. The user thus has some concrete elements to show the eye care professional that there probably is a problem with the optical lenses. This should avoid users not coming back because thinking they are responsible for the problem. The detailed results of the suitability assessment can also provide useful information to the eyecare professional (ECP) so that, in case the user of the optical device cannot adapt to this equipment, the eyecare professional can choose a more suitable design of progressive addition lenses (PAL) or other type of lens for the user.

According to another example, when the suitability index is under the predetermined threshold value, a refined test can also be provided, for example by computer program so as to better understand the cause of non-adaptation. The refined test can be for example:
- a test of visual acuity for near vision or far vision to check if refraction is correct.
- questions about activity of the user in order to check if the activity is compatible with the use of the optical lenses of the optical device, The predetermined threshold value can be the same for everyone or determined based on information relative to the user, for example the age, the size, the arms' length, the correction . . . .

It can also be based on previous recordings, for example level of comfort with a previously used optical device.

The predetermined threshold value may be determined from a distribution of suitability index provided by different users having the same profile and equipment: For instance, for new wearer of progressive addition lens, who previously were wearing single vision lens and being myopics may have a specific distribution for index. Knowing this distribution, one can identify people having indicator representing less than 5% of population, as being people who have problem with the optical device. It is thus possible to build threshold from the previously expressed indicators, and so have more accurate threshold.

Moreover, the method can further comprise an information providing step S18, during which information is provided to a professional based on the result of the comparing step S14. Advantageously, the method can further comprise a second comparison step S20 and an alert providing step S22.

During the step S20, if the assessed suitability index is much lower than the predetermined threshold value, the assessed suitability index is compared to a critical threshold value.

Then, an alert is provided to the user and/or to a professional or any access means to the professional based on the result of the second comparing step during the step S22.

For example, the professional is an eye care professional (ECP) or an eyeglasses manufacturer.

In the claims, the word "comprising" does not exclude other elements or steps, and the indefinite article "a" or "an" does not exclude a plurality. The mere fact that different features are recited in mutually different dependent claims does not indicate that a combination of these features cannot be advantageously used. Any reference signs in the claims should not be construed as limiting the scope of the invention.

The invention claimed is:

1. A method, implemented by a computer, for assessing a suitability between an optical device and a user of the optical device, the optical device including at least an optical lens configured to be placed in front of at least an eye of the user when the user uses the optical device, the at least optical lens having a plurality of optical zones having different optical functions, the method comprising:
   requesting the user, equipped with the optical device, to use the optical device in a plurality of different visual situations, each of the visual situations being associated with an optical zone of the optical lens and during which the user looks at a visual target located in a natural environment of the user through the optical lens;
   receiving an assessed suitability index assessed by the user based on a use of the user of the optical device in the plurality of different visual situations;
   comparing the assessed suitability index to a predetermined threshold value;
   providing a recommendation to the user based on one or more of a result of the comparing and the evolution over time of the assessed suitability index, the provided recommendation provided to the user comprising data on how to suitably use the optical device;
   comparing the assessed suitability index to a critical threshold value when the assessed suitability index is lower than the predetermined threshold value; and
   providing an alert to one or more of the user and a professional based on the result of the comparing the assessed suitability index to the critical threshold value.

2. The method according to claim 1, further comprising:
   repeating the requesting and the receiving the assessed suitability index at least on a weekly basis; and
   storing the evolution over time of the assessed suitability index.

3. The method according to claim 1, wherein the receiving the assessed suitability index comprises receiving a subjective assessment related to one or more of:
   a level of comfort of the user during the use of the optical device in the plurality of different visual situations,
   a level of fatigue of the user during the use of the optical device in the plurality of different visual situations, and
   a level of difficulty of the user to use the optical device in the plurality of different visual situations.

4. The method according to claim 1, wherein the receiving the assessed suitability index comprises measuring a physiological parameter indicative of the physiology of the user during the use of the optical device in the plurality of different visual situations.

5. The method according to claim 1, wherein the receiving the assessed suitability index comprises determining a level of visual performance of the user during the use of the optical device in the plurality of different visual situations.

6. The method according to claim 5, wherein the receiving the assessed suitability index comprises determining an environmental parameter relative to the parameter of the natural environment of the user during the use of the optical device in the plurality of different visual situations, and
   wherein the level of visual performance of the user is determined based on the environmental parameter.

7. The method according to claim 1, wherein for each different visual situation of the plurality of different visual situations, the user equipped with the optical device is requested to use the optical device during a predetermined duration.

8. The method according to claim 1, wherein the request is one or more of generated and sent by a remote unit.

9. The method according to claim 1, wherein the optical device is one of the ophthalmic devices comprising:
   a progressive addition lens,
   a bifocal lens,
   a multifocal lens,
   a mid-distance lens,
   a lens having a tint gradient,
   an augmented reality eyewear, and
   a single vision lens having different astigmatism correction for near and far visions.

10. A non-transitory computer-readable medium on which is stored a computer program comprising one or more stored sequences of instructions that are accessible to a processor and which, when executed by the processor, causes the processor to carry out the method of claim 1.

11. The method according to claim 2, wherein the receiving the assessed suitability index comprises receiving a subjective assessment related to one or more of:
- a level of comfort of the user during the use of the optical device in the plurality of different visual situations,
- a level of fatigue of the user during the use of the optical device in the plurality of different visual situations, and
- a level of difficulty of the user to use the optical device in the plurality of different visual situations.

12. The method according to claim 2, wherein the receiving the assessed suitability index comprises measuring a physiological parameter indicative of the physiology of the user during the use of the optical device in the plurality of different visual situations.

13. The method according to claim 3, wherein the receiving the assessed suitability index comprises measuring a physiological parameter indicative of the physiology of the user during the use of the optical device in the plurality of different visual situations.

14. The method according to claim 2, wherein the receiving the assessed suitability index comprises determining a level of visual performance of the user during the use of the optical device in the plurality of different visual situations.

* * * * *